United States Patent [19]

Migdal et al.

[11] Patent Number: 4,962,142
[45] Date of Patent: Oct. 9, 1990

[54] REACTIVE, NON-YELLOWING TRIAZINE COMPOUNDS USEFUL AS UV SCREENING AGENTS FOR POLYMERS

[75] Inventors: Cyril A. Migdal; John B. Hines, both of Spartanburg; Edward W. Kluger, Pauline, all of S.C.

[73] Assignee: Milliken Research Corporation, Spartanburg, S.C.

[21] Appl. No.: 270,871

[22] Filed: Nov. 14, 1988

Related U.S. Application Data

[62] Division of Ser. No. 139,342, Dec. 29, 1987, Pat. No. 4,826,978.

[51] Int. Cl.$^5$ .................. C08K 5/3492; C08F 8/00; C08G 18/32
[52] U.S. Cl. .................................... 524/100; 525/132; 525/398; 525/460; 528/85; 528/254; 528/332; 528/418
[58] Field of Search ............... 524/100; 525/132, 398, 525/460; 528/85, 254, 332, 418

[56] References Cited

U.S. PATENT DOCUMENTS

| | | | |
|---|---|---|---|
| 3,244,708 | 4/1966 | Duennenberger | 544/216 |
| 3,268,474 | 8/1966 | Hardy et al. | 524/100 |
| 4,619,956 | 10/1986 | Susi | 524/87 |
| 4,801,508 | 1/1989 | Lutz et al. | 524/100 |
| 4,826,978 | 5/1989 | Migdal et al. | 544/216 |

*Primary Examiner*—Kriellion Morgan

*Attorney, Agent, or Firm*—Terry T. Moyer; H. William Petry

[57] ABSTRACT

Triazine compounds are disclosed which are useful for imparting UV screening properties to polymers of the formula:

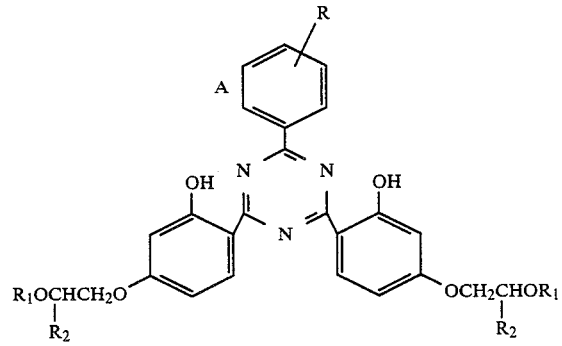

wherein R is an electron withdrawing group; $R_1$ is H,

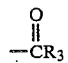

where $R_3$ is an alkyl group having from one to about six carbon atoms; and $R_2$ is selected from H and $CH_3$, also disclosed are polymer compositions having improved UV screening properties containing said triazine compounds.

1 Claim, No Drawings

REACTIVE, NON-YELLOWING TRIAZINE COMPOUNDS USEFUL AS UV SCREENING AGENTS FOR POLYMERS

This is a division of application Ser. No. 139,342, filed Dec. 29, 1987, now U.S. Pat. No. 4,826,978.

The present invention relates to triazine compounds useful for imparting UV (ultraviolet) screening properties to polymers. More particularly, the present invention relates to non-yellowing triazine compounds and polymer compositions.

Many products such as fruit juices, soft drinks, drinks, food products, cosmetics and shampoos are deleteriously affected by UV light when packaged in clear plastic containers which pass significant portions of the available light at any wavelength from approximately 300 to 400 nm. By use of the triazine compounds of the present invention polymeric containers may be manufactured which absorb these harmful wavelengths and therefore reduce or eliminate the UV light degradation of products packaged therein.

The triazine compounds of the present invention may also be useful for providing UV screening properties in films and coatings, especially coatings to be used for outdoor applications such as automobiles, aircraft, buildings, etc.

Commercially available UV stabilizers for coatings may tend to diffuse out of the coating or become extracted from the coating by, for instance, detergents or solvents. Because such coatings, however, are cross-linked using conventional crosslinking agents, it has been found that the present triazine compounds may react with the crosslinking materials thus becoming permanently bonded to the coating. Because they are bonded to the coating, they may be nonextractable and less subject to diffusion out of the coating.

The present triazine compounds are thermally stable and generally nonsublimable at the processing temperatures normally encountered for the application end uses described above, e.g., films, coatings and beverage and food containers.

A further advantage of the present triazine compounds is that they may impart UV stabilization to the conventional additives used in food and beverage containers and bottles and in films and coatings, such as colorants, pigments, fillers, brighteners and the like.

The triazine compounds of the present invention offer the further advantage of being relatively non-yellowing as compared to known triazine compounds of the type, for instance, disclosed in U.S. Pat. No. 3,244,708 (Ciba-Geigy) and U.S. Pat. No. 4,619,956 (American Cyanamid) and in European patent application No. 165,608 (Ciba-Geigy). The present triazine compounds, furthermore, may be relatively non-yellowing both in a pure (nonreacted) and reacted form.

In accordance with the present invention, certain triazine compounds defined below are provided, said compounds having the formula:

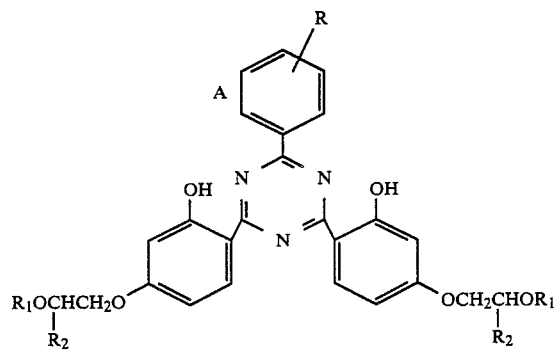

wherein R is an electron withdrawing group; $R_1$ is H,

where $R_3$ is an alkyl group having from one to six carbon atoms; and is $R_2$ selected from H and $CH_3$. Preferably the electron withdrawing groups selected for the R position may include halogen, cyano, trifluoromethyl, nitro, and acetoxy. Even more preferably R is halogen, e.g., chlorine, bromine and fluorine.

Also contemplated by the present invention is a polymer composition which comprises a polymer having reacted therein a total of from about 0.05 to about 5, preferably from about 0.1 to about 2 percent by weight based upon the weight of the polymers of at least one UV absorbing compound of the formula:

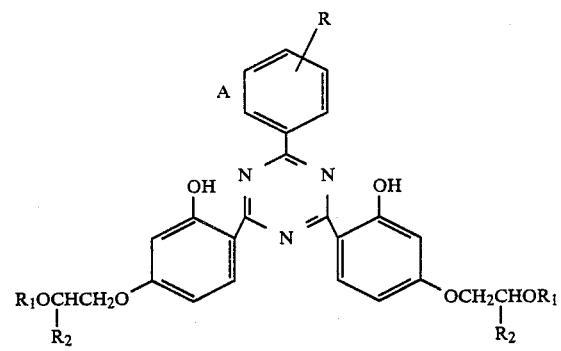

As mentioned above, the polymers which may be stabilized against the deleterious effects of UV light according to the present invention include a wide range of polymers made by condensation reactions and addition reactions. Polymers made by condensation reaction may include, for instance, alkyds, the aminos, e.g., melamine and urea, epoxies, phenolics, polycarbonates, polyesters, and silicones. With regard to such condensation polymers the triazines may be reacted therewith through a reactive hydroxyl group on the triazine compound or the reaction may be through a reactive ester group on the triazine by means of a transesterification reaction.

Particularly preferred condensation polymers include linear, thermoplastic molding polymers such as polyesters, copolyether esters (such as Hytrel® made by DuPont) and polycarbonates. Polyester, fiber grade polymers may also be preferred.

Suitable polymers made by addition reaction include, for instance, polyurethanes and epoxy resins.

The triazine compounds of the present invention may also have significant applications as a UV screening agent for coatings, especially exterior coatings where degradation of the coating due to UV exposure may be a problem. In this application area the triazine compound also becomes bound and may be, hence, non-sublimable and non-extractable. In the case of cured coatings, such as reactive acrylics cross-linked with melamine-formaldehyde, urea-formaldehyde or isocyanates, the triazine compounds may become bonded to the coating during crosslinking where the compounds react with the crosslinking agents conventionally employed in such coatings. In two-part urethane coatings, where an isocyanate is reacting with a polyol or polyamine to form the final polymeric coating, the triazine becomes bound into the final polymer through reaction with the isocyanate. In the case of other coating systems, such as alkyds and unsaturated polyesters, the triazine compounds are bonded into the polymer during the original polymerization step and the polymers are then cured conventionally by a free radical mechanism.

As to the non-yellowing feature of the compounds of the present invention, it will be apparent to those skilled in the art that such a feature may be particularly advantageous where yellowing of the product cannot be tolerated. Why the compounds of the present invention exhibit this non-yellowing feature is not fully understood. However, while not being limited to any particular theory, it is theorized that the present triazines may be non-yellowing due to the presence of the electron-withdrawing group on the phenyl ring (ring A in the structure) of the triazine molecule Substitution on the ortho or para position of ring A may be preferred. Most preferred is the para position.

The electron withdrawing group, it is theorized, may reduce the basicity of the triazine molecule which may render it less susceptible to degradation and resultant yellowing.

The present invention may be further understood by reference to the following examples which are not to be construed as limiting the scope of the subject matter of the invention in any way. Unless otherwise indicated all parts or percentages are by weight.

EXAMPLE 1

Synthesis of 2,4-bis[2-hydroxy-4-(2-hydroxyethoxy)-phenyl]-6-(4-chlorophenyl)-1,3,5-triazine A slurry of cyanuric chloride (500 g, 2.71 mol) and aluminum chloride (800 g, 6.01 mol) in chlorobenzene (2.4 L) was maintained at 125° C. for 18 hours under nitrogen. The mixture was cooled to room temperature and then poured into ice water (4 L). A steam distillation of the quenched reaction mixture removed chlorobenzene. The crude product was collected by filtration and dried. The crude product identified below was recrystallized from acetonitrile: mp 149°–150° C.

2,4-dichloro-6-(4-chlorophenyl)-1,3,5-triazine    (I)

A slurry of compound I (425 g, 1.64 mol) and resorcinol (365 g, 3.31 mol) in nitrobenzene (2.4 L) was cooled to 10° C. under nitrogen. Then, with efficient cooling, aluminum chloride (500 g, 3.75 mol) was added over 1 hour. The slurry was allowed to warm up to room temperature and stir for 16 hours, followed by heating for 4 hours at 50° C. After cooling to room temperature, the mixture was poured into ice water (4 L) containing HCl (100 mL). Next, the slurry was washed with water until pH 2. A steam distillation of the washed slurry removed nitrobenzene. The crude product was collected by filtration and dried. The crude product identified below was recrystallized from N,N-dimethylformamide-water. mp>300° C.

2,4-bis(2,4-dihydroxyphenyl)-6-(4-chlorophenyl)-1,3,5-triazine    (II)

A slurry of compound II (100 g, 0.25 mol) in ethoxyethanol (750 mL) was warmed to 40° C. Then, potassium carbonate (40 g, 0.29 mol) was added and the mixture was heated to reflux under nitrogen. Next, 2-chloroethanol (80 mL, 1.19 mol) was added dropwise over 12 hours. An additional quantity of potassium carbonate (40 g, 0.26 mol) was added in several portions to maintain a pH of 9 throughout the 2-chloroethanol addition. The mixture was cooled to room temperature and the precipitate that formed was collected by filtration. The crude product was washed with water, collected by filtration and dried. The crude product identified below was recrystallized from 1,4-dioxane: mp 232°–234° C.; UV-absorption (ethyl benzoate) $\lambda_{max}=359$ nm, $*E_{max}=74$.

Analysis calculated for $C_{25}H_{22}ClN_3O_6$: C, 60.55; H, 4.47; Cl, 7.15; N, 8.47; 0, 19.36.

Found: C, 60.30; H, 4.59; Cl, 6.91; N, 8.44; 0, 19:55.

2,4-bis[2-hydroxy-4-(2-hydroxyethoxy)-phenyl]-6-(4-chlorophenyl)-1,3,5-triazine    (III)

EXAMPLE 2

Preparation Of The Corresponding Ester

A slurry of compound III (10 g, 0.02 mol) and p-toluenesulfonic acid (0.3 g, 0.002 mol) in acetic anhydride (100 mL) was heated under nitrogen up to 70° C. in 15 minutes. When the slurry dissolved, the solution was cooled to room temperature. Then, the mixture was quenched in pH 9 water. The precipitate was collected by filtration and dried. The crude product identified below was recrystallized from ethyl acetate: mp 138°–140° C.;

UV-absorption (N,N-dimethylformamide) $\lambda_{max}=352$ nm, $*E_{max}=62$.

Analysis calculated for $C_{29}H_{26}ClN_3O_8$: C,60.05; H, 4.52; Cl, 6.11; N, 7.24; 0, 22.06.

Found: C, 60.08; H, 4.51; Cl, 7.17; N, 7.06; 0, 21.41.

2,4-bis[2-hydroxy-4-(2-acetoxyethoxy)-phenyl]-6-(4-chlorophenyl)-1,3,5-triazine    (IV)

EXAMPLE 3

Comparative Example

A dry reactor under nitrogen was charged with tetrahydrofuran (500 mL) and cyanuric chloride (90 g, 0.49 mol). Then, 2M phenyl magnesium chloride in tetrahydrofuran (275 mL) was slowly added over 4 hours. The mixture was warmed to 40° C. and was left to stir overnight. The tetrahydrofuran was then removed by vacuum distillation. To the remaining mixture was added nitrobenzene (500 mL) and resorcinol (78 g, 0.71 mol). The mixture was cooled to 10° C. Then, with efficient cooling, aluminum chloride (100 g, 0.75 mol) was added over 30 minutes. The mixture was then heated for 24 hours at 50° C. After cooling to room temperature, the mixture was poured into ice water (4 L) containing HCl (100 mL). Next, the slurry was washed with water until pH 2. A steam distillation of the washed slurry removed nitrobenzene. The crude product identified below was collected by filtration and dried.

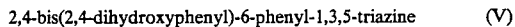

2,4-bis(2,4-dihydroxyphenyl)-6-phenyl-1,3,5-triazine    (V)

A slurry of compound V (100 g, 0.27 mol) in ethoxyethanol (750 mL) was warmed to 40° C. Then, potassium carbonate (40 g, 0.29 mol) was added and the mixture was heated to reflux under nitrogen. Next, 2-chloroethanol (100 mL, 1.49 mol) was added dropwise over 12 hours. An additional quantity of potassium carbonate (60 g, 0.43 mol) was added in several portions to maintain a pH of 9 throughout the 2-chloroethanol addition. The mixture was cooled to room temperature and the precipitate that formed was collected by filtration. The crude product was washed with water, collected by filtration and dried. The crude product identified below was recrystallized from 1,4-dioxane: mp 250°-252° C.; UV-absorption (ethyl benzoate) $\lambda_{max}=358$ nm, $*E_{max}=78$.

Analysis calculated for $C_{25}H_{23}N_3O_6$: C, 65.07; H, 5.02; N, 9.11; 0, 20.80.

Found: C, 64.93; H, 5.09; N, 9.03; 0, 21.30.

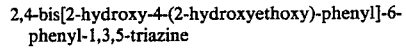

2,4-bis[2-hydroxy-4-(2-hydroxyethoxy)-phenyl]-6-phenyl-1,3,5-triazine    (VI)

EXAMPLE 4

Comparative Example

A slurry of cyanuric chloride (80 g, 0.43 mol), m-xylene (60 mL, 0.49 mol), and aluminum chloride (100 g, 0.75 mol) in chlorobenzene (500 mL) was stirred under a nitrogen blanket. Next, the slurry was maintained at 40° C. for 4 hours, followed by cooling to room temperature overnight. The slurry was poured into hexanes (1.5 L). The hexanes layer was decanted away from a black oil. Next, ice water (3 L) was added to the black oil resulting in a white precipitate. The crude product identified below was collected by filtration. It was washed with acetone (500 mL).

2,4-dichloro-6-(2,4-dimethylphenyl)-1,3,5-triazine    (VII)

A slurry of compound VII (138 g, 0.55 mol) and resorcinol (120 g, 1.10 mol) in nitrobenzene (1 L) was cooled to 10° C. under nitrogen. Then, with efficient cooling, aluminum chloride (250 g, 1.88 mol) was added over 30 minutes. The slurry was allowed to warm up to room temperature and stir for 16 hours. The mixture was poured into ice water (4 L) containing HCl (100 mL). Next, the slurry was washed with water until pH 2. The crude product was collected by filtration and then washed in hexanes. The crude product was collected again by filtration and dried. The crude product identified below was recrystallized from N,N-dimethylformamide-water: mp>300° C.

2,4-bis(2,4-dihydroxyphenyl)-6-(2,4-dimethylphenyl)-1,3,5-triazine    (VIII)

A slurry of compound VIII (50 g, 0.12 mol) in ethoxyethanol (400 mL) was warmed to 40° C. Then, potassium carbonate (20 g, 0.14 mol) was added and the mixture was heated to reflux under nitrogen. Next, 2-chloroethanol (30 mL, 0.45 mol) was added dropwise over 12 hours. An additional quantity of potassium carbonate (7 g, 0.05 mol) was added in several portions to maintain a pH of 9 throughout the 2-chloroethanol addition. The mixture was cooled to room temperature and the precipitate that formed was collected by filtration. The crude product was washed with water, collected by filtration and dried. The crude product identified below was recrystallized from methyl ethyl ketone: mp 204°-207° C.; UV-absorption (N-N-dimethylformamide) $\lambda_{max}=351$ nm, $*E_{max}=84$.

Analysis calculated for $C_{27}H_{27}N_3O_6$: C, 66.25; H, 5.56; N, 8.58; 0, 19.60.

Found C, 66.14; H, 5.59; N, 8.46; 0, 19.78.

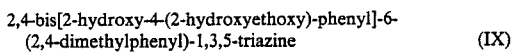

2,4-bis[2-hydroxy-4-(2-hydroxyethoxy)-phenyl]-6-(2,4-dimethylphenyl)-1,3,5-triazine    (IX)

EXAMPLE 5

A slurry of cyanuric chloride (100 g, 0.54 mol) and aluminum chloride (175 g, 1.31 mol) in bromobenzene (450 mL) was maintained at 120° C. for 24 hours under nitrogen. The mixture was cooled to room temperature and then poured into ice water (2 L). A steam distillation of the quenched reaction mixture removed bromobenzene. The crude product was collected by filtration and dried. The dried crude product identified below was recrystallized from acetonitrile: mp 161°-163° C.

2,4-dichloro-6-(4-bromophenyl)-1,3,5-triazine    (X)

A slurry of compound X (74 g, 0.25 mol) and resorcinol (60 g, 0.55 mol) in nitrobenzene (500 mL) was cooled to 10° C. under nitrogen. Then, with efficient cooling, aluminum chloride (125 g, 0.94 mol) was added over 30 minutes. The slurry was allowed to warm up to room temperature and stir for 16 hours, followed by heating for 4 hours at 50° C. After cooling to room temperature, the mixture was poured into ice water (3 L) containing HCl (50 mL). Next, the slurry was washed with water until pH 2. A steam distillation of the washed slurry removed nitrobenzene. The crude product was collected by filtration and dried. The crude product was recrystallized from N,N-dimethylformamide-water: mp>300° C.

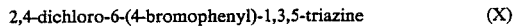

2,4-bis(2,4-dihydroxyphenyl)-6-(4-bromophenyl)-1,3,5-triazine    (XI)

A slurry of compound XI (55 g, 0.12 mol) in ethoxyethanol (400 mL) was warmed to 90° C. Then, potassium carbonate (20 g, 0.15 mol) was added and the mixture was heated to reflux under nitrogen. Next, 2-chloroethanol (42 mL, 0.63 mol) was added dropwise over 12 hours. An additional quantity of potassium carbonate (22 g, 0.16 mol) was added in several portions to maintain a pH of 9 throughout the 2-chloroethanol addition. The mixture was cooled to room temperature and the precipitate that formed was collected by filtration. The crude product was washed with water, collected by filtration and dried. The crude product identified below was recrystallized from 1,4-dioxane-acetone: mp 222°-224° C.; UV-absorption (N,N-dimethylformamide) $\lambda_{max}=352.5$ nm, $*E_{max}=66$.

Analysis calculated for $C_{25}H_{22}BrN_3O_6$: C, 55.56; H, 4.10; Br, 14.78; N, 7.77; O, 17.76.

Found: C, 55.44; H 4.14; Br, 14.14; N, 7.64; O, 18.81.

2,4-bis[2-hydroxy-4-(2-hydroxyethoxy)-phenyl]-6-(4-bromophenyl)-1,3,5-triazine (XII)

* The absorptivity, $E_{max}$, is related to the extinction coefficient ($\epsilon$) by $E_{max} \times M = \epsilon$ where M is the molecular weight of the UV-absorber.

EXAMPLE 6

The Non-Yellowing Characteristic of Solid Compound III versus Other Mixed Triazine Compounds.

One gram of Compounds II, III, IV, IX, and XII were each separately slurried in aliquots of boiling ethoxyethanol (25 mL). Each slurry was coated while hot on stainless steel plates. The ethoxyethanol was allowed to evaporate into the air. The resulting coatings were approximately 4 mil thick.

The plates were the exposed in the Hanau Xenotest 1200 for 48 hours at 63° C. and 50% relative humidity. The change in color was measured by a Hunter Lab-Scan II Color Difference Meter. The color difference observed represents a change in yellow and is denoted by the symbol $\Delta b$.

TABLE I

Yellowing of Pure Triazines Upon Exposure to UV-Light in Accelerated Weathering

| UV-Absorber | Hours of Exposure | $\Delta b$ |
| --- | --- | --- |
| Compound II | 48 | +1.8 |
| Compound III | 48 | −0.2 |
| Compound VI | 48 | +5.3 |
| Compound IX | 48 | +11.5 |
| Compound XII | 48 | −0.3 |

EXAMPLE 7

Preparation of Poly(ethylene terephthalate) Containing UV-Absorber

For the preparation of poly(ethylene terephthalate) reacted with Compound III, the following chemicals are placed in a flask:

| dimethyl terephthalate | 97.0 parts |
| --- | --- |
| ethylene glycol | 62.0 parts |
| metal catalyst | 0.04 part |

The flask is equipped with a nitrogen inlet, stirrer, vacuum outlet, and condenser. The flask and contents are heated slowly to 210° C. at which time 0.01 part of phosphorous catalyst is added. When the temperature reaches 230° C. 0.5 part of Compound III is added to the flask. Next, the pressure is reduced and the temperature increased until the vacuum is 0.02 mm Hg and temperature is 285° C. The polymer condensation is complete within 1 hour at these conditions. When the flask is cooled; the resulting polymer is clear yellow. An experiment of this type resulted in a polymer which when molded into a film absorbed UV-light between 250–400 nm. It was also found that addition of Compound III did not affect the kinetics of the polymer condensation, nor did it sublime out of or discolor the poly(ethylene terephthalate) resin significantly.

EXAMPLE 8

Preparation of Coatings Containing UV-Absorbers

An extraction study was carried out on crosslinked acrylic enamels containing Compound III and competitive UV-absorbers to determine if they were extractable. Stock solutions of Compound III, Tinuvin 900[1], Tinuvin 1130[2], and 2-(2H-benzotriazol-2-yl)-5-methoxyphenol were made by dissolving the UV-absorber (0.3 g) in N,N-dimethylformamide (10 mL). The samples were made by adding 1 mL aliquots from each stock solution to separate portions of Acryloid AT-51[3] (4 g). The resin samples were placed in separate aluminum weighing dishes and allowed to air dry for 2 hours. They were then cured at 120° C. for 3 hours producing a hard enamel. After cooling to room temperature, the samples were broken into small pieces and soaked in N,N-dimethylformamide for two days. High Pressure Liquid Chromatography analysis of the N,N-dimethylformamide solutions indicated that Tinuvin 900[1] and 2-(2H-benzotriazol-2-yl)-5-methoxyphenol were extracted from the samples, but Compound III and Tinuvin 1130[2] were not extracted. Evidently, the primary aliphatic hydroxy substituents on Compound III and Tinuvin 1130[2] react with the hydroxymethyl melamine crosslinker, binding the stabilizer to the enamel.

Footnotes

1. Tinuvin 900 is a high molecular weight substituted benzotriazole UV-absorber manufactured by Ciba-Geigy Corp.

2. Tinuvin 1130 is a reactive substituted benzotriazole UV-absorber manufactured by Ciba-Geigy Corp.

3. Acryloid AT-51 is a hydroxy substituted acrylic resin manufactured by Rohm and Haas and containing a hydroxymethyl melamine cross-linker.

EXAMPLE 9

The Non-Yellowing Characteristics of a Coating Containing Bound Compound III versus Coatings Containing Other Bound Triazine Compounds A yellowing study was carried out on coatings containing Compound III and other reactive triazine compounds. Stock solutions of Compound III, Compound VI, and Compound IX were made by dissolving 0.6 grams of each compound in N,N-dimethylformamide (100 mL). Three coating resins were made by adding 5 mL of stock solution to 6 grams of Acryloid AT-51[3] coating resin. A fourth coating resin was made by adding 5 mL N, N-dimethylformamide to 6 grams Acryloid AT-51[3] resin. Aliquots of 6 grams from each coating resin were cast as coatings onto white ceramic tiles using a #20 drawdown rod. The coatings were cured at 120° C. overnight. The coatings were placed in the Hanau Xenotest 1200 at 63° C. and 50% relative humidity The color change was measured at intervals using a Hunter Labscan II Color Difference Meter. The color difference observed represents a change in yellow and is denoted by the symbol $\Delta b$. The values for $\Delta b$ are listed in Table 2.

TABLE 2

Yellowing of Coatings Containing UV-Absorbers Upon Exposure to UV-Light in Accelerated Weathering

| UV-Absorber | Hours Of Exposure | $\Delta b$ |
| --- | --- | --- |
| Compound III | 238 | 0.0 |

TABLE 2-continued

Yellowing of Coatings Containing UV-Absorbers Upon Exposure to UV-Light in Accelerated Weathering

| UV-Absorber | Hours Of Exposure | Δb |
|---|---|---|
| No Stabilizer | 238 | 0.2 |
| Compound VI | 238 | 0.6 |
| Compound IX | 238 | 0.3 |

EXAMPLE 10

Extraction Study of Poly(ethylene terephthalate) Resin Containing UV-Absorber

Poly(ethylene terephthalate) resins containing 5000 and 7500 ppm of Compound III were prepared in a similar manner to that described in Example 7. Exactly 0.2 grams of each batch of the resin was mixed with spectroscopy grade N,N-dimethylformamide (100 mL) for 15 minutes at 100° C. Analysis of the liquid extract by High Pressure Liquid Chromatography and UV spectroscopy showed that no significant amount of Compound III was present in the extract. Samples were extracted in duplicate and spiked for confirmation.

We claim:

1. A polymer composition stabilized against the deleterious effects of UV light which comprises a polymer having reacted therein a total of from about 0.05 to about 5 percent by weight of at least one UV absorbing compound of the formula:

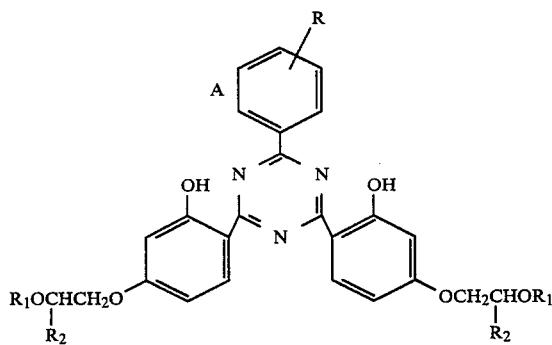

where R is an electron withdrawing group; $R_1$ is H,

where $R_3$ is an alkyl group having from one to 6 carbon atoms; and $R_2$ is selected from H and $CH_3$.

2. The polymer composition of claim 1 wherein R is selected from halogens, cyano, trifluoromethyl, nitro or acetoxy.

3. The polymer composition of claim 2 wherein R is selected from chlorine, bromine and fluorine.

4. The polymer composition of claim 1 wherein the polymer is a condensation polymer selected from alkyds, aminos, phenolics, polyesters, polycarbonates, copolyether esters or silicones.

5. The polymer composition of claim 1 wherein the polymer is an addition polymer selected from epoxies or urethanes.

6. A coating composition stabilized against UV light, which comprises: a polymer wherein from about 0.05 to about 5 percent parts by weight of a triazine compound has been reacted into said coating, said triazine compound having the formula:

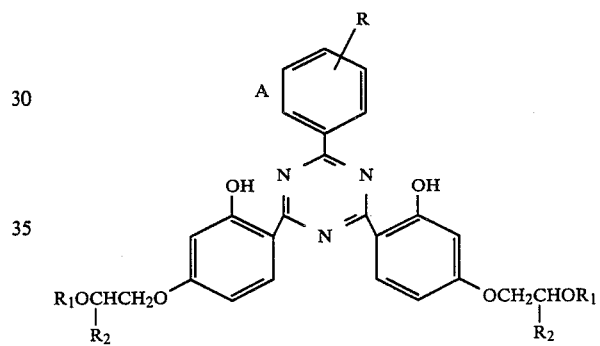

7. The coating composition of claim 6 wherein said coating is a cured coating and said triazine compound has been reacted with crosslinking agents selected from melamine-formaldehyde, urea formaldehyde, or isocyanates employed to cure said coatings.

* * * * *